United States Patent [19]

Desbois

[11] 4,205,195

[45] May 27, 1980

[54] PROCESS FOR THE DIMERIZATION OF $C_8$-$C_{20}$ OLEFINS AND THE OLEFIN DIMERS OBTAINED THEREBY

[75] Inventor: Michel Desbois, Rillieux, France

[73] Assignee: Rhone-Poulenc Industries, Paris, France

[21] Appl. No.: 23,288

[22] Filed: Mar. 23, 1979

[30] Foreign Application Priority Data

Mar. 28, 1979 [FR] France .................................. 79 08852

[51] Int. Cl.$^2$ ............................................... C07C 3/10
[52] U.S. Cl. ..................................... 585/510; 585/520
[58] Field of Search ................................ 585/510, 520

[56] References Cited

U.S. PATENT DOCUMENTS

| | | | |
|---|---|---|---|
| 2,462,360 | 2/1949 | Carnell | 585/520 |
| 2,563,051 | 8/1951 | Linn | 585/520 |
| 2,656,303 | 10/1953 | Lee et al. | 585/520 |
| 2,830,106 | 4/1958 | Good et al. | 585/510 |
| 3,422,162 | 1/1969 | Oldham et al. | 585/520 |
| 3,953,538 | 4/1976 | Boney | 585/313 |

Primary Examiner—C. Davis

[57] ABSTRACT

$C_8$–$C_{20}$ olefins are dimerized in the presence of hydrofluoric acid, by (1) contacting for about 1 to 30 minutes, at least one $C_8$–$C_{20}$ olefin with liquid hydrofluoric acid at a temperature of between about $-20°$ C. and $+60°$ C., in a molar ratio of hydrofluoric acid to olefin of between about 1:1 and 50:1; (2) immediately after the contacting, the hydrofluoric acid present is removed almost instantaneously from the dimerization medium; (3) a defluorination of the said medium is effected; and (4) the resultant oledimers are recovered.

12 Claims, No Drawings

PROCESS FOR THE DIMERIZATION OF $C_8$-$C_{20}$ OLEFINS AND THE OLEFIN DIMERS OBTAINED THEREBY

BACKGROUND OF THE INVENTION

The present invention relates to a new process for the dimerization of $C_8$–$C_{20}$ olefins in the presence of hydrofluoric acid, as well as to the olefin dimers thus obtained.

It has been proposed (U.S. Pat. No. 2,830,106) to dimerize $C_6$–$C_{15}$ olefins, particularly α-olefins, in the presence of a catalyst having a base of activated alumina containing 0.5 percent to 3 percent by weight of hydrofluoric acid. Such a process has numerous drawbacks, namely, only a low rate of conversion of the olefin is obtained, with a very low yield of dimers, and the preparation of the catalyst is very complicated.

By the present invention, a new process has been discovered of dimerizing olefins in the presence of hydrofluoric acid which does not present these disadvantages.

It is an object of the present invention to provide a new process for the dimerization of olefins which overcomes the disadvantages of the prior art.

It is another object of the present invention to provide a process for the dimerization of olefins providing higher rates of conversion of the olefins and permitted by the prior art and to provide higher yields of dimers.

It is a further object of the invention to provide the olefin dimers produced by the process of the invention.

Other objects will be apparent to those skilled in the art from the present description.

GENERAL DESCRIPTION OF THE INVENTION

In the dimerization process of the invention, a $C_8$-$C_{20}$ olefin is dimerized in the presence of liquid hydrofluoric acid by (1) contacting the olefin monomer for between about 1 to 30 minutes, and preferably, from about 5 to 20 minutes, at a temperature of between about $-20°$ C. to $+60°$ C., and preferably, between about 0° and 40° C., in a molar ratio of hydrofluoric acid to olefin of between about 1:1 and 50:1, and preferably, between about 3:1 and 30:1; (2) immediately after the said contacting almost and substantially instantaneously separating the hydrofluoric acid present from the dimerization medium; (3) effecting a defluorination of the said medium; and (4) recovering the resultant olefin dimers.

The process of the invention can be carried out continuously or batchwise. The continuous method is, however, preferred.

The process of the invention is particularly valuable and preferable for the dimerization of $C_{10}$-$C_{16}$ α-olefins, such as 1-decene, 1-dodecene, 1-tetradecene, and 1-hexadecene.

The contacting step of the process is effected with rapid agitation, for instance, by means of an agitator of the turbine or worm type, preferably under a pressure of from about 5 to 10 bars.

The step (2), above, of the substantially instantaneous separation of the hydrofluoric acid immediately after the contacting, can be carried out, for instance, by rapid distillation of the "flash vaporization" type from the dimerization medium in order to eliminate the free liquid hydrofluoric acid in vapor form, or by neutralization of the dimerization medium by conventional agents for the neutralization of hydrofluoric acid, such as potassium hydroxide in aqueous solution.

The defluorination step (3) can be effected, for instance, by stripping, i.e., by extraction at a temperature above about 200° C. by means of a saturated aliphatic or an aromatic hydrocarbon which is inert with respect to the hydrofluoric acid, of the type of dodecane, di-tert-butylbenzene, xylene, etc. This step can also be effected by treatment with alumina at a temperature of between about 50° C. and 250° C. In this way there is obtained a mixture of oligomers containing a major portion of dimers and possibly a small amount of non-oligomerized olefin, which can be eliminated by simple distillation.

The removal of the dimers (4) from the mixture of oligomers can be effected by distillation.

The process for the dimerization of $C_8$-$C_{20}$ olefins of the present invention makes it possible to obtain olefin dimers in high yields. Thus, this process, carried out with a time of contact between the hydrofluoric acid and the olefin of preferably between about 5 and 20 minutes, makes it possible to obtain olefin dimers in a yield of more than about 60 percent.

These olefin dimer products have the conventional uses of long-chain olefins.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Into a double-jacketed 400 cc. reactor, with strong agitation, the temperature of which is controlled and regulated at about 20° C., there are introduced, by means of metering pumps, 1-tetradecene at a rate of 1.4 liters per hour and anhydrous hydrofluoric acid at the rate of 1 liter per hour, which corresponds to a molar ratio of acid to olefin of 9 and a time of contact of 10 minutes.

The reaction mixture which emerges continuously from this reactor is brought, for a very short time (a few seconds), to a temperature of 100° C. to 140° C., so as to eliminate in gaseous form the major part of the hydrofluoric acid present.

The compounds which have been treated in this manner are then collected in a vessel containing 10 percent aqueous potassium hydroxide, intended to trap the last traces of free hydrofluoric acid. After this mixture has been decanted and dried over calcium chloride, there is obtained the non-defluorinated crude compound, whose composition, as determined by chromatographic analysis (gel permeation) and measurement of the fluorine content, is as follows:

|  | Percent by Weight |
|---|---|
| Non-oligomerized olefin | 2.7 |
| Fluorotetradecane | 1.3 |
| Olefin dimer | 52.0 |
| Fluoride of the $C_{14}$ olefin dimer | 26.0 |
| Heavier compounds (corresponding trimers, | |

-continued

|  | Percent by Weight |
|---|---|
| tetramers and fluorides) | 18.0 |

This mixture is then subjected to defluorination by stripping with dodecane at 215° C. to give a defluorinated compound having the following composition:

|  | Percent by Weight |
|---|---|
| Non-oligomerized olefin | 4 |
| Olefin dimer | 81 |
| Heavier products | 15 |

EXAMPLE 2

The method described in Example 1 is carried out with the following conditions:

| Nature of the olefin | 1-dodecene |
|---|---|
| Temperature | 0° C. |
| Rate of introduction of the olefin | 1.28 liters per hour |
| Rate of introduction of the hydrofluoric acid | 3.52 liters per hour |
| Molar ratio of hydrofluoric acid to olefin | 30 |
| Contact time | 5 minutes |

A defluorinated finished product is obtained of the composition:

|  | Percent by Weight |
|---|---|
| Non-oligomerized olefin | 2 |
| Olefin dimer | 65 |
| Heavier products | 33 |

EXAMPLE 3

The method described in Example 1 is carried out with the following conditions:

| Nature of the olefin | 1 hexadecene |
|---|---|
| Temperature | 40° C. |
| Rate of introduction of the olefin | 0.99 liter per hour |
| Rate of introduction of the hydrofluoric acid | 0.21 liter per hour |
| Molar ratio of hydrofluoric acid to olefin | 3 |
| Contact time | 20 minutes |

A defluorinated finished product is obtained having the following composition:

|  | Percent by Weight |
|---|---|
| Non-oligomerized olefin | 7 |
| Olefin dimer | 74 |
| Heavier products | 19 |

EXAMPLE 4

The method described in Example 1 is carried out with the following conditions:

| Nature of the olefin | 1-decene |
|---|---|
| Temperature | 0° C. |
| Rate of introduction of the olefin | 0.32 liter per hour |
| Rate of introduction of the hydrofluoric acid | 0.88 liter per hour |
| Molar ratio of hydrofluoric acid to olefin | 30 |
| Contact time | 20 minutes |

A defluorinated finished product is obtained whose composition is as follows:

|  | Percent by Weight |
|---|---|
| Non-oligomerized olefin | 2 |
| Olefin dimer | 58 |
| Heavier products | 40 |

EXAMPLE 5

(Comparative)

The operation described in Example 1 is carried out with a long contact time under the following conditions:

| Nature of the olefin | 1-tetradecene |
|---|---|
| Temperature | 40° C. |
| Rate of introduction of the olefin | 0.35 liter per hour |
| Rate of introduction of the hydrofluoric acid | 0.25 liter per hour |
| Molar ratio of hydrofluoric acid to olefin | 9 |
| Contact time | 40 minutes |

There is obtained a defluorinated finished product whose composition is as follows:

|  | Percent by Weight |
|---|---|
| Non-oligomerized olefin | 20 |
| Olefin dimer | 26 |
| Heavier products | 54 |

EXAMPLE 6

(Comparative)

A contacting step is carried out as in Example 1 with the following conditions:

| Nature of the olefin | 1-tetradecene |
|---|---|
| Temperature | 30° C. |
| Rate of introduction of the olefin | 1.4 liter per hour |
| Rate of introduction of the hydrofluoric acid | 1 liter per hour |
| Molar ratio of hydrofluoric acid to olefin | 9 |
| Contact time in the reactor | 10 minutes |

The reaction mixture thus obtained is then passed into a 4.5 liter settling vessel where it stays for about 2 hours.

The organic phase discharging from this settling vessel is brought, for a very brief period of time (a few seconds), to a temperature of 100° C. to 140° C., so as to eliminate the major part of the hydrofluoric acid in gaseous form.

The medium is then subjected to the defluorination and separation operations described in Example 1.

A defluorinated finished product is obtained whose composition is as follows:

|  | Percent by Weight |
|---|---|
| Non-oligomerized olefin | 25 |
| Olefin dimer | 20 |
| Heavier products | 55 |

EXAMPLE 7

A contacting operation of olefin monomer and hydrofluoric acid absolutely in accordance with that described in Example 1 is carried out.

The reaction mixture which continuously leaves the reactor in which the contacting has been effected is immediately collected in a 20 percent aqueous solution so as almost immediately to trap the hydrofluoric acid in the form of potassium fluoride.

The defluorination and separation operations are then carried out as in Example 1.

|  | Percent by Weight |
|---|---|
| Non-oligomerized $C_{14}$ olefin | 10 |
| $C_{14}$ olefin dimer | 67 |
| Heavier products | 23 |

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process of dimerizing $C_8$–$C_{20}$ olefins in the presence of hydrofluoric acid, comprising:

(1) contacting for about 1 to 30 minutes at least one $C_8$–$C_{20}$ olefin with liquid hydrofluoric acid at a temperature of between about $-20°$ C. and $+60°$ C. in a molar ratio of hydrofluoric acid to olefin of between about 1:1 and 50:1;
    (2) immediately after the contacting operation, substantially instantaneously separating the hydrofluoric acid present from the dimerization medium;
    (3) effecting a defluorination of said medium; and
    (4) recovering the resultant olefin dimers.

2. A process according to claim 1, wherein the said contacting operation is carried out for about 5 to 20 minutes at a temperature of between about 0° and 40° C. in a molar ratio of hydrofluoric acid to olefin of between about 3:1 and 30:1.

3. A process according to claim 1, wherein said step of substantially instantaneously separating the hydrofluoric acid immediately after the contacting operation is effected by rapid distillation.

4. A process according to claim 3, wherein said rapid distillation is flash distillation.

5. A process according to claim 1, wherein the said operation of substantially instantaneously separating the hydrofluoric acid immediately after the contacting operation is effected by neutralization of the dimerization medium with a neutralization agent for the neutralization of hydrofluoric acid.

6. A process according to claim 5, wherein the neutralization agent is potassium hydroxide in aqueous solution.

7. A process according to claims 1, 2, 3, 4, 5, or 6, wherein the olefin is a $C_{10}$–$C_{16}$ α-olefin.

8. A process according to claim 1, wherein the olefin is 1-decene.

9. A process according to claim 1, wherein the olefin is 1-dodecene.

10. A process according to claim 1, wherein the olefin is 1-tetradecene.

11. A process according to claim 1, wherein the olefin is 1-hexadecene.

12. A dimer obtained in accordance with the process of any of claims 1 to 6.

* * * * *